United States Patent
Tripp, Jr. et al.

(10) Patent No.: US 6,635,020 B2
(45) Date of Patent: Oct. 21, 2003

(54) REUSABLE FLUID PRESSURE TRANSDUCER MONITORING APPARATUS

(75) Inventors: Carl F. Tripp, Jr., Salt Lake City, UT (US); Mark A. Christensen, Salt Lake City, UT (US); Eric Simon, Salt Lake City, UT (US)

(73) Assignee: Thermometrics, Salt Lake City, UT (US)

(*) Notice: Subject to any disclaimer, the term of this patent is extended or adjusted under 35 U.S.C. 154(b) by 242 days.

(21) Appl. No.: 09/892,155

(22) Filed: Jun. 26, 2001

(65) Prior Publication Data

US 2002/0198458 A1 Dec. 26, 2002

(51) Int. Cl.⁷ .......................... A61B 5/021; A61B 5/02; A61B 5/00
(52) U.S. Cl. .......................... 600/488; 73/1.57; 73/721; 73/756; 116/200; 116/283; 116/284; 600/486; 600/487; 600/561
(58) Field of Search .................. 73/1.57, 1.58, 73/708, 715, 717, 719, 720, 721, 731, 756, 1.66, 1.67; 600/485, 486, 488, 561, 487; 116/200, 266, 271, 272, 276, 281, 283, 284

(56) References Cited

U.S. PATENT DOCUMENTS

| | | | | |
|---|---|---|---|---|
| 3,610,228 A | * | 10/1971 | Temkin | 600/486 |
| 4,227,420 A | * | 10/1980 | Lamadrid | 73/756 |
| 4,545,389 A | * | 10/1985 | Schaberg et al. | 600/561 |
| 4,576,181 A | * | 3/1986 | Wallace et al. | 600/488 |
| 4,658,829 A | * | 4/1987 | Wallace | 600/561 |
| 4,683,894 A | * | 8/1987 | Kodama et al. | 600/488 |
| 4,920,972 A | | 5/1990 | Frank et al. | 128/675 |
| 4,970,900 A | * | 11/1990 | Shepherd et al. | 73/756 |
| 5,097,841 A | * | 3/1992 | Moriuchi et al. | 73/708 |
| 5,273,047 A | * | 12/1993 | Tripp et al. | 600/488 |
| 5,335,551 A | * | 8/1994 | Ohnishi et al. | 600/488 |
| 5,417,395 A | * | 5/1995 | Fowler et al. | 604/151 |
| 5,522,266 A | * | 6/1996 | Nicholson et al. | 73/708 |
| 5,551,300 A | * | 9/1996 | Vurek et al. | 73/708 |
| 5,566,676 A | * | 10/1996 | Rosenfeldt et al. | 600/485 |
| 5,711,302 A | * | 1/1998 | Lampropoulos et al. | 600/561 |
| 5,752,918 A | * | 5/1998 | Fowler et al. | 600/488 |
| 5,848,971 A | * | 12/1998 | Fowler et al. | 600/486 |
| 5,868,678 A | | 2/1999 | Brunner et al. | 600/486 |
| 5,993,395 A | | 11/1999 | Shulze | 600/488 |
| 6,056,697 A | * | 5/2000 | Owens et al. | 600/485 |
| 6,117,086 A | | 9/2000 | Shulze | 600/488 |

OTHER PUBLICATIONS

Brochure for Disposable Biotrans# Snap–On Dome Kits, BioSensors International Pte Ltd.
Brochure for Logical# Pressure Transducer System, Medex.

* cited by examiner

Primary Examiner—George L. Walton
(74) Attorney, Agent, or Firm—Workman Nydegger Seeley (57) ABSTRACT

An apparatus for monitoring fluid pressure includes a reusable base section, and a disposable dome section detachably connected to the base section. The disposable dome section defines a fluid pathway and includes a dome viewing segment in fluid communication with a flush segment and a stopcock segment. A pressure transducer sensor is disposed in the reusable base section and is adapted to produce electrical signals proportional to fluid pressures sensed in the fluid pathway. A usage indicator can be disposed in the base section to provide a visual indication of usage of the apparatus within a predetermined number of uses. A calibration port can be provided in the base section to allow for simple calibration by the user without violating the sterility of the apparatus. The ability to reuse the base section with the sensor component reduces the cost of the apparatus, while the disposability of the dome section with the fluid pathway ensures sterility for each use.

46 Claims, 8 Drawing Sheets

REUSABLE FLUID PRESSURE TRANSDUCER MONITORING APPARATUS

BACKGROUND OF THE INVENTION

1. Field of the Invention

The present invention relates generally to a transducer system for the measurement of blood pressure or other fluid pressure. In particular, the present invention relates to a fluid pressure transducer apparatus that incorporates reusable sensor components with disposable fluid path components, and which is easily calibrated for accurate fluid pressure monitoring.

2. Background Technology

For many medical applications, it is important to monitor bodily fluid pressures such as blood pressure. There are generally two types of methods used for measuring and/or monitoring blood pressure, namely indirect and direct methods. Indirect measurements are based on non-invasive procedures such as using a pressure cuff and a stethoscope. Direct pressure measurements are, in contrast, made by using invasive techniques that have the advantages of providing more accurate, more continuous, and if desired, more localized pressure monitoring.

For direct blood pressure measurement and monitoring, typically a catheter is inserted into a blood vessel and is connected to tubing that in turn is connected to a pressure transducer. The transducer includes a sensor that senses the pressure of the fluid path and converts the pressure therein to electrical signals which correspond to the quantity of pressure. The electrical signals are transmitted to a monitor and/or other output devices that display the patient's blood pressure.

With rising health care costs there has been a drive towards developing more cost-effective devices for measuring blood pressure. This has led to the development of disposable blood pressure transducers. Disposable systems typically include a pressure sensor, cable, plastic housing, stopcock, flush device, and associated tubing which are assembled together and provided to the hospital or medical care provider in a sterile package. Such a system is intended for a single patient use, following which the entire assembly is disposed of. The average manufacturing cost of this type of system is fairly high, with the pressure sensor and cable representing the two most costly components. Therefore, any improvements in this type of system with the aim of reduced costs will tend to focus on these two components, specifically evaluating the necessity of disposing this portion of the system following each use.

Reusable transducer systems have been developed that comprise a two-component system in which the relatively expensive sensor on a faceplate is reusable, while the other component with the patient-contacting fluid path is disposable. In these types of systems, each component is provided with a diaphragm that closes off access to the fluid path and the sensor, respectively. In order to measure pressure in the fluid path, the disposable component is attached to the reusable faceplate component with the diaphragms in a confronting and pressure communicating relationship to thereby communicate pressure from the fluid path to the sensor. These two-component transducer systems typically have the disposable fluid path component, usually referred to as the fluid dome, rotatably coupled to the reusable sensor portion. The components are typically secured together by threaded interaction to bring the diaphragms into confronting and pressure communicating relationship by relative rotation between the dome and the reusable component and their respective diaphragms. After use, the disposable unit is removed from the reusable part and discarded, and may be replaced with a new and sterile unit.

Examples of blood pressure measuring devices that are reusable are described in U.S. Pat. Nos. 5,752,918; 5,868,678; 4,920,972; 5,993,395; and 6,117,086. There are also commercially available reusable blood pressure measuring devices such as the LogiCal™ transducer system manufactured by Medex, and the BioTrans™ transducer system manufactured by Biosensors International. These systems have addressed the problems of cost containment through reuse of the sensor and cable; however, all of these systems generally exhibit the following problems: (1) unpredictable failure time due to an unspecified life cycle of the reusable faceplate; (2) inventory level management problems as a result of the unspecified reusable life cycle; (3) sensor inaccuracy and calibration costs; (4) lack of a convenient calibration method for the end user; and (5) obstructed fluid path visibility in the region of the disposable/reusable diaphragm interface.

More specifically, regarding the first problem described above, there are limitations to the expected lifetime of the reusable faceplate component which are caused by wear associated with multiple disposable dome attachments to the reusable faceplate, particularly in the location of the disposable dome interface with the reusable sensor. The lifetime of the device is also limited by the effects of material degradation from alcohol or detergent cleansing of the reusable faceplate and sensor diaphragm surface following each use. Unpredictable failure of the reusable component is a serious problem in medical applications where a patients' lives are frequently in jeopardy.

The second problem described above concerns the inventory management problems that can arise from a blood transducer device having an unknown reusable component lifetime. A hospital or medical care provider may overstock the replacement faceplates to ensure the availability of these components. This approach, however, counteracts the cost advantages of using a reusable system due to the need to carry excessive inventory. Alternatively, the possibility of not carrying sufficient inventory may result in the loss of a critical device in an emergency situation.

The third problem described above is associated with sensor accuracy and calibration costs. Current iterations of the two component reusable systems use a sensor module identical to those used in traditional disposable systems, which have been pre-calibrated to meet the performance specifications of the disposable systems. A shift in sensor performance is typically observed following assembly of the sensor into the reusable package. The reusable system manufacturer is able to correct for some of the performance shifts that occur following packaging, but usually does not have the expertise required to adjust all of the affected parameters. As a result, these manufacturers are frequently confronted with yield losses associated with out of specification performance and/or non-optimized performance. Furthermore, each sensor must be re-calibrated on an individual basis after packaging into the device housing, which greatly increases costs and time required for individual testing of each assembled device.

The fourth problem with prior systems concerns the difficulties in calibration or functionality tests for an end user. The traditional calibration methods have usually been either (1) front side pressure application; (2) back side pressure application; or (3) electronic calibration. Front side calibration typically consists of attaching a pressure generating device such as a syringe to the fluid filled side of the transducer and monitoring the transducer output for proper response. The disadvantages of front side calibration are that the system must be primed with fluid prior to the test, and that the pressure mechanism must interact with the sterile fluid pathway, which requires significant effort to ensure that the fluid pathway is not contaminated. Back side calibration differs from front side calibration by applying pressure to the non-sterile side of the transducer, which avoids the problems of sterility violation and is the method currently utilized by several manufacturers.

Electronic calibration and functionality testing are performed without the use of a pressure source. A resistive network is interconnected with the electronic circuitry of the sensor and/or cable via a user operated switch which creates a predictable change in the sensor's output. This method has the advantage of eliminating any need for a pressure generating device, but only tests the electrical connectivity of the system, as opposed to the front and back side testing which include a mechanical exercising of the diaphragm, thereby providing a more thorough testing of functionality. One of the current devices on the market, the Medex LogiCal™ system, can be tested through front side calibration and also incorporates an electronic calibration test switch with the reusable portion of the device. This approach has the disadvantage of incurring additional costs in the reusable component through the inclusion of a user activated switch and an additional resistor, plus the associated wiring.

The fifth problem associated with prior two-component reusable fluid pressure monitoring systems arises from the inability to view the fluid path in the area directly above the interface of the reusable sensor and the disposable dome. Initially, the system needs to be filled with saline solution and air bubbles must be eliminated prior to patient use. Air bubbles in the system not only degrade the accuracy of the device as a result of unwanted signal dampening, but also present a significant safety problem for the patient. For example, the introduction of air into the cardiovascular system may result in possible embolism. An area of particular concern is the area surrounding the disposable dome and reusable sensor interface. This area tends to contain an uneven surface between the diaphragms that promotes the formation of bubbles and also inhibits the flushing out of these bubbles during the saline solution fill operation. The reusable sensor diaphragms in the LogiCal™ transducer system and the BioTrans™ transducer system are circular, with input and output ports positioned in the area of the reusable to disposable dome interface, thus obstructing visibility in the most critical areas of air bubble formation.

Therefore, there is a need for a reusable blood pressure transducer system that overcomes the above problems and disadvantages.

SUMMARY AND OBJECTS OF THE INVENTION

It is a primary object of the invention to provide a system for the direct measurement of fluid pressure that includes a disposable dome component and a reusable base component.

Another object of the invention is to provide a blood pressure monitoring apparatus having a usage indicator which is advanced with each disposable dome attachment and intended to provide a visual indication of reusable base usage within a qualified number of uses, thereby avoiding the problem of unpredictable failure due to an unspecified lifetime for a reusable component.

A further object of the invention is to provide a reusable pressure transducer that is accurate, and inexpensive to manufacture and calibrate.

It is yet another object of the invention to provide a reusable blood pressure monitoring apparatus that enhances fluid flow visibility in the region of the disposable dome to reusable sensor interface to aid the user in assuring air bubble elimination during the system saline fill process.

It is a further object of the invention to provide a reusable blood pressure monitoring apparatus having a self-registering hinge and latch interface between the disposable and reusable components which is ergonomically beneficial to the user.

Another object of the invention is to provide a reusable blood pressure monitoring apparatus having a calibration port through which pressure may be applied to the sensing element for calibration/functionality testing without contacting the sterile disposable component of the apparatus.

To achieve the forgoing objects, and in accordance with the invention as embodied and described herein, an apparatus is provided for fluid pressure monitoring in medical applications such as monitoring of blood pressure. The apparatus includes a reusable base section, and a disposable dome section detachably connected to the base section and adapted to be coupled to a patient. The disposable dome section defines a fluid pathway and includes a dome viewing segment in fluid communication with a flush segment and a stopcock segment. The disposable dome and associated diaphragm have a geometry such that the input and output ports are sufficiently far from the critical viewing area to greatly enhance the fluid flow visibility in the fluid pathway, thereby reducing the risk of introducing harmful air bubbles into a patient's bloodstream.

A pressure transducer sensor is disposed in the reusable base section and is adapted to produce electrical signals proportional to fluid pressures sensed in the fluid pathway. The design of the pressure sensor ensures accuracy and minimal calibration of the device. A usage indicator is disposed in the base section to provide a visual indication of usage of the apparatus within a predetermined number of uses. This allows the operator to determine whether or not the number of uses of the apparatus is within the specified recommended limit. A calibration port can be provided in the base section to allow for simple calibration by the user without violating the sterility of the apparatus. The ability to reuse the base section with the sensor component reduces the cost of the apparatus, while the disposability of the dome section with the fluid pathway ensures sterility for each patient use.

These and other objects and features of the present invention will become more fully apparent from the following description, or may be learned by the practice of the invention as set forth hereinafter.

BRIEF DESCRIPTION OF THE DRAWINGS

In order to more fully understand the manner in which the above recited and other advantages and objects of the invention are obtained, a more particular description of the invention briefly described above will be rendered by reference to specific embodiments thereof which are illustrated in the appended drawings. Understanding that these drawings depict only typical embodiments of the invention and are not therefore to be considered limiting of its scope, the invention will be described and explained with additional specificity and detail through the use of the accompanying drawings in which.

DETAILED DESCRIPTION OF THE INVENTION

The present invention is directed to a system for the direct monitoring of fluid pressure such as blood pressure in a patient. In particular, the present invention is a reusable blood pressure transducer monitoring apparatus that incorporates a reusable pressure sensing portion and a disposable fluid path portion, and which is easily calibrated for accurate blood pressure monitoring in a patient.

Figure 1:
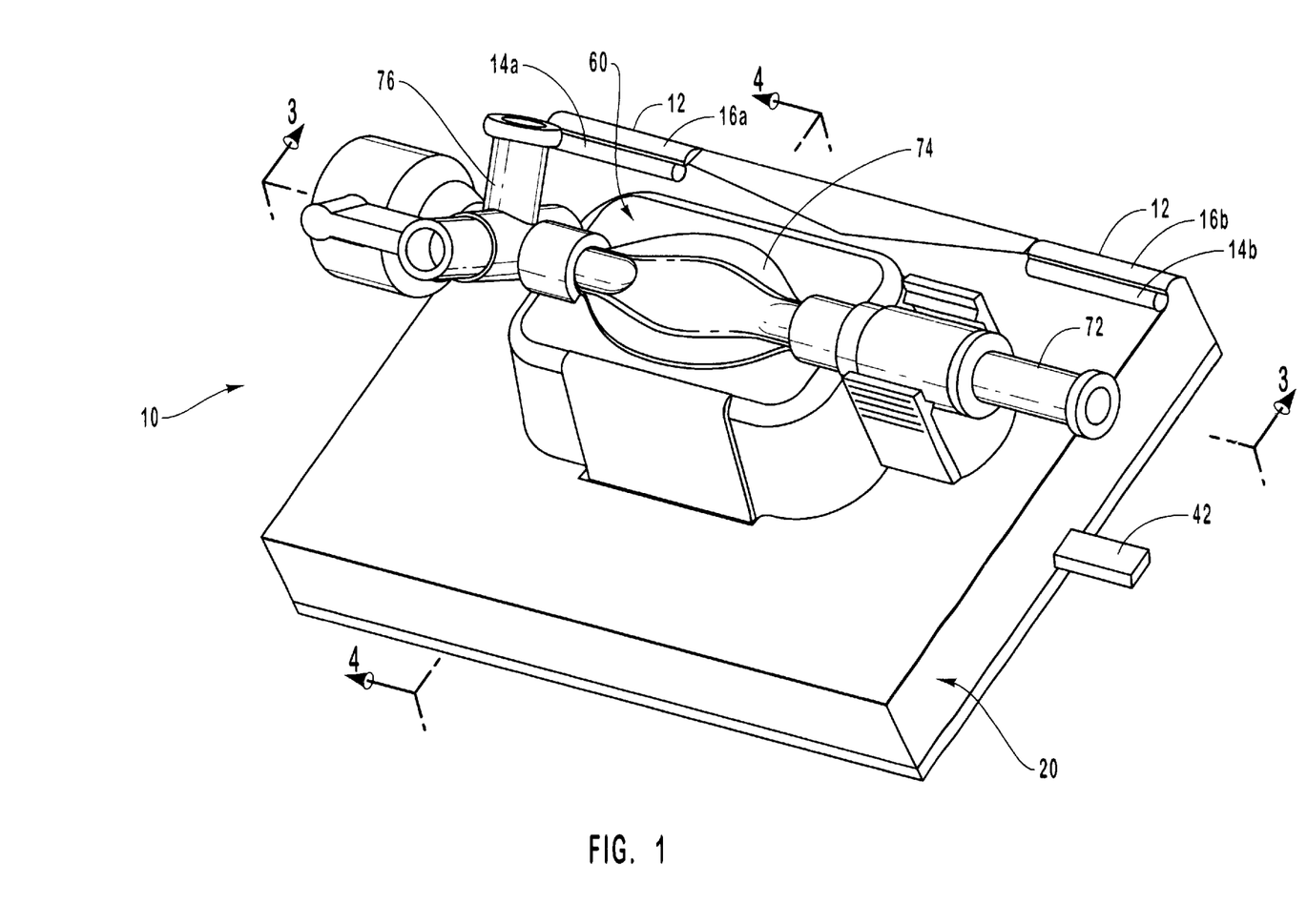
FIGS. 1 and 2 are perspective views of a blood pressure monitoring apparatus in accordance with one embodiment of the present invention.
Figure 2:
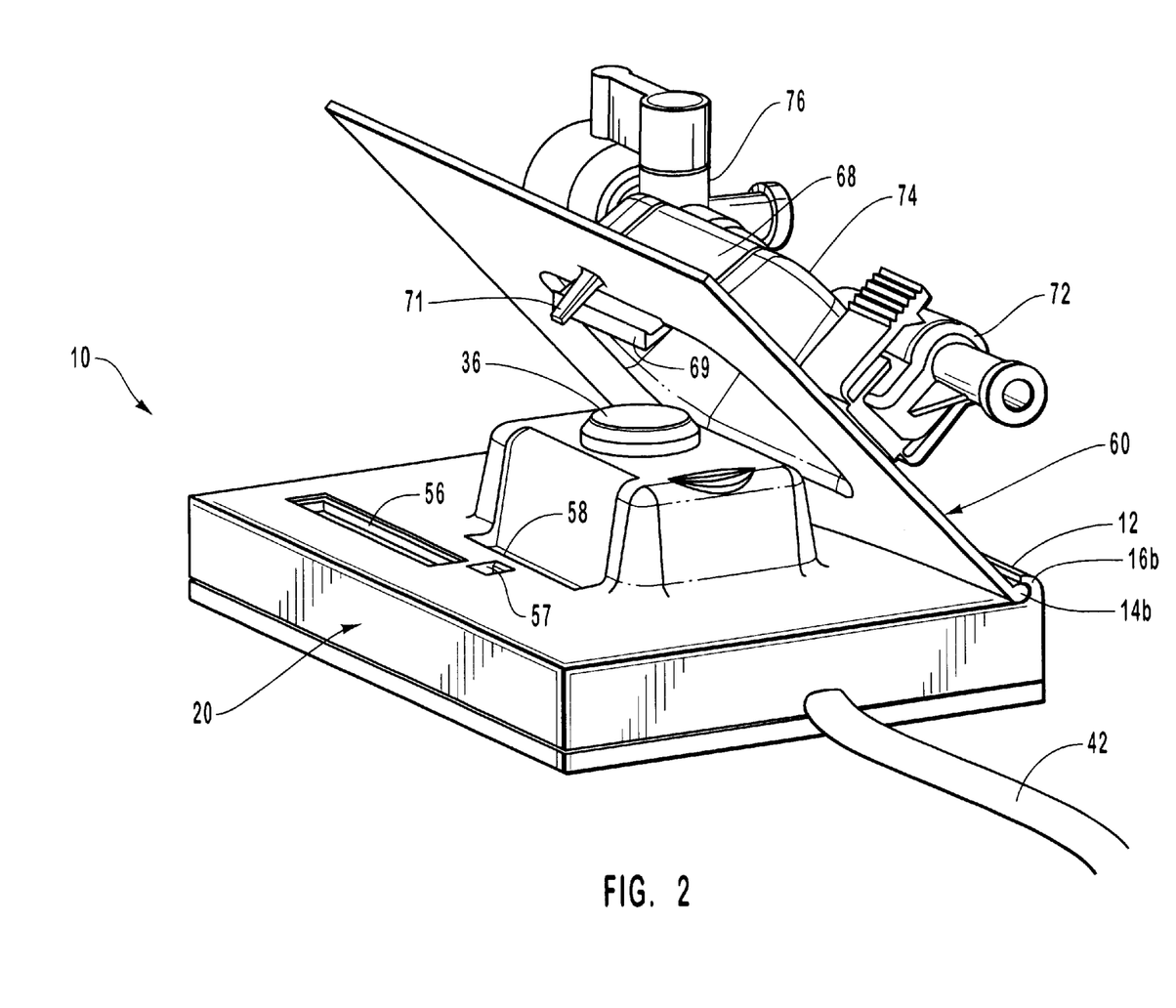

Referring to the drawings, wherein like structures are provided with like reference designations, FIGS. 1 and 2 are perspective views of a blood pressure monitoring apparatus 10 in accordance with one embodiment of the present invention. The monitoring apparatus 10 generally comprises two major parts which are releasably interconnected together, including a reusable base section 20 and a disposable dome section 60, which is detachable from base section 20 and is generally intended for one time use. FIG. 1 shows monitoring apparatus 10 in a closed position and ready for use. FIG. 2 depicts monitoring apparatus 10 in an open position, which occurs during removal of a used dome section or during attachment of a new dome section for future use.

In one embodiment, reusable base section 20 and disposable dome section 60 are releasably interconnected by a releasable hinge structure 12. The hinge structure 12 includes a pair of hinge rods 14a and 14b that are formed on one edge of dome section 60. The hinge rods 14a and 14b are configured to releasably couple with a pair of curved ridges 16a and 16b formed on one edge of base section 20. It will be appreciated by those skilled in the art that other conventional hinge constructions can also be used for hinge structure 20.

Figure 3:
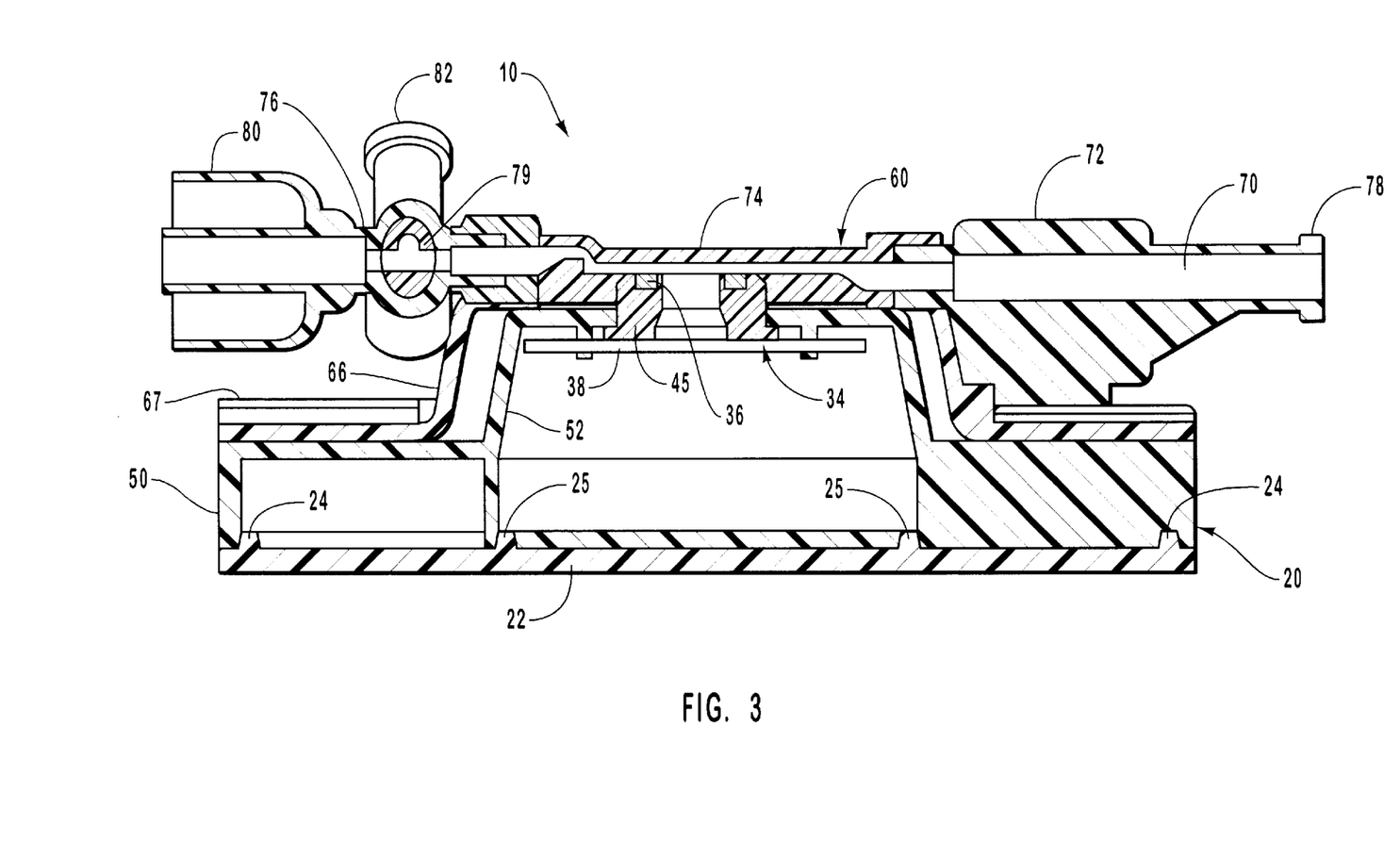
FIG. 3 is a longitudinal cross-sectional side view of the blood pressure monitoring apparatus of FIG. 1 taken along line 3—3 thereof.
Figure 4:
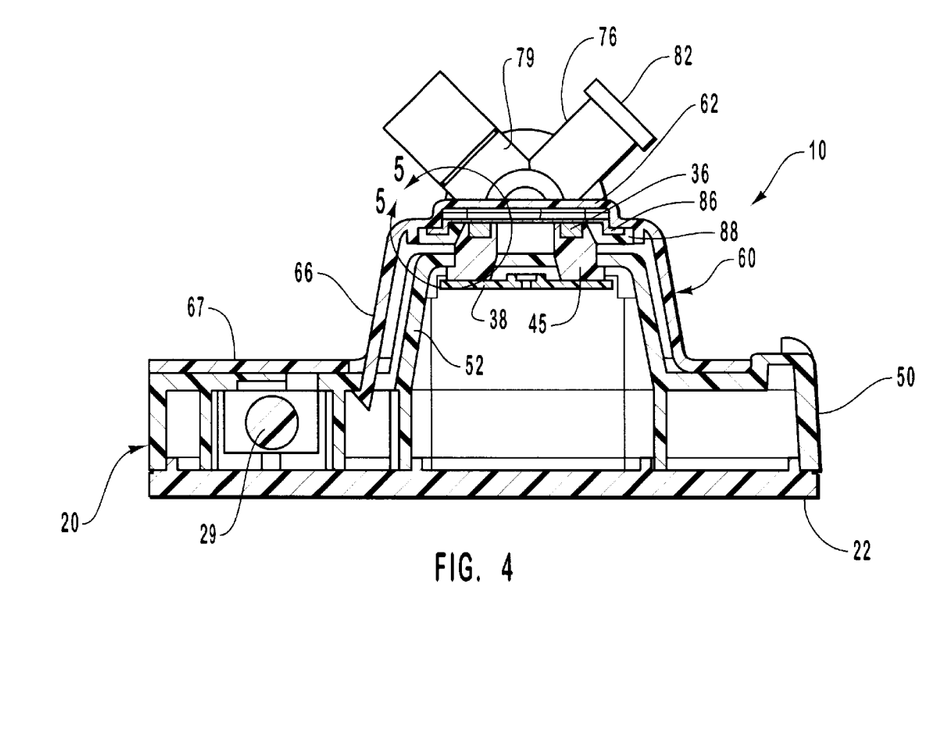
FIG. 4 is a lateral cross-sectional side view of the blood pressure monitoring apparatus of FIG. 1 taken along line 4—4 thereof.

FIG. 3 is a longitudinal cross-sectional side view of monitoring apparatus 10 taken along line 3—3 of FIG. 1, which is shown in the closed position for operation of the device. FIG. 4 is a lateral cross-sectional side view of monitoring apparatus 10 taken along line 4—4 of FIG. 1. A fluid pathway 70 extends through dome section 60 as shown most clearly in FIG. 3. The fluid pathway 70 is defined by a flush segment 72, a dome viewing segment 74, and a stopcock segment 76, each of which include channel portions that communicate one with another to provide fluid pathway 70. Each of these segments of dome section 60 will be discussed in further detail hereafter.

Figure 6:
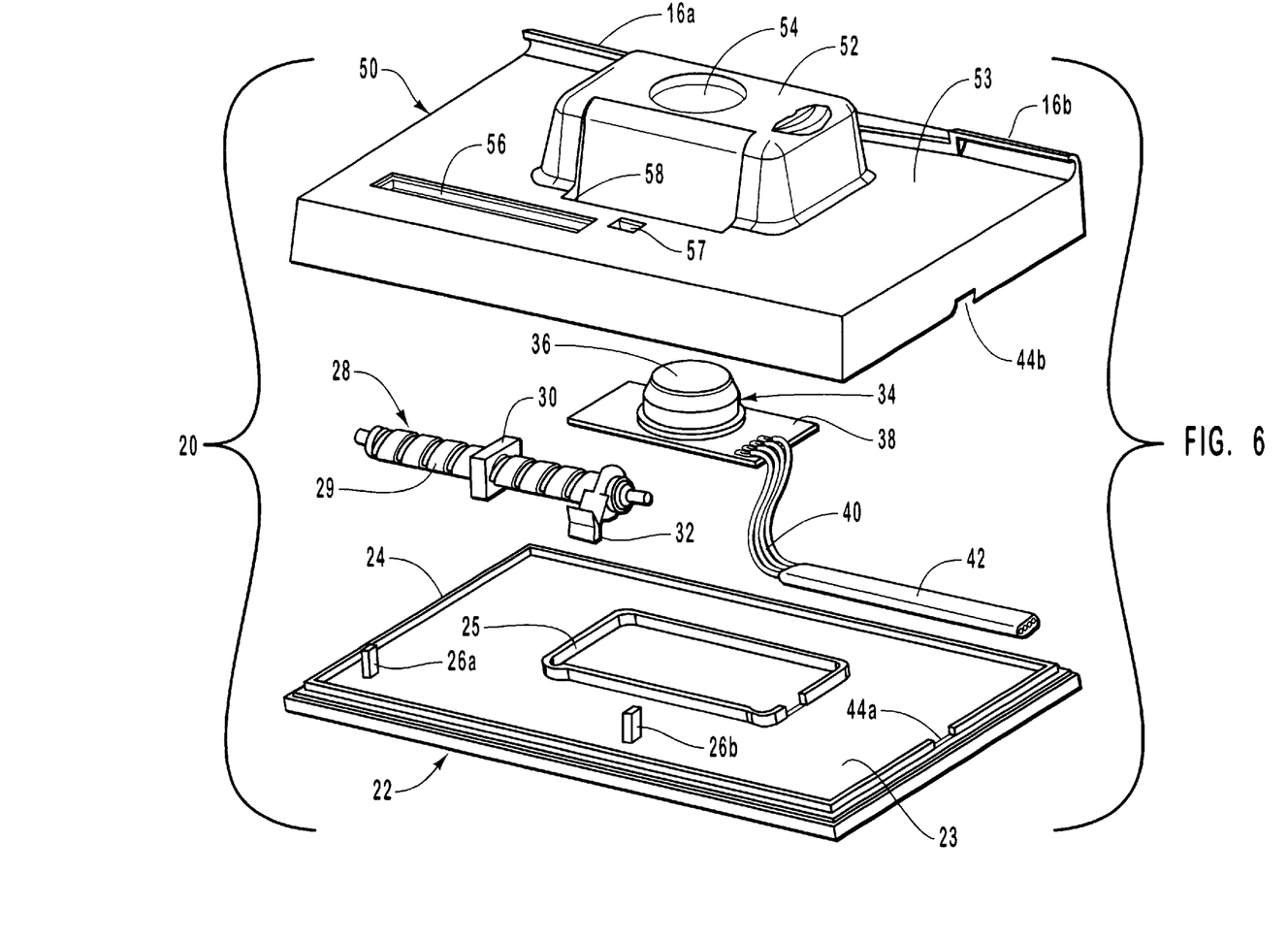
FIG. 6 is an exploded view of the reusable base section of the blood pressure monitoring apparatus of FIG. 1.

FIG. 6 is an exploded view of reusable base section 20. The base section 20 has a reusable back plate 22 and a reusable face plate 50, which are interconnected to form a housing structure for base section 20. The back plate 22 and face plate 50 are preferably formed from unitary pieces that are, for example, injection molded from medical grade plastic material. The back plate 22 has a generally rectangular shape with an inner planar surface 23 and is configured to interconnect with face plate 50 through an outer ridge 24 formed on the periphery of surface 23. An inner ridge 25 is formed on surface 23 and is adapted to provide an additional surface for attachment of face plate 50. The interconnections of outer ridge 24 and inner ridge 25 with faceplate 50 are particularly shown in FIG. 3.

A pair of protrusions 26a and 26b are formed on surface 23 and are configured to mate with grooves formed on the underside of faceplate 50 for holding a mechanical usage indicator 28 in place. The usage indicator 28 is one example of a means for indicating usage of the device. The usage indicator 28 includes a threaded cylindrical push rod 29 on which is spring loaded an indicator nut 30 that is used to provide visual indication of the number of uses of the device. A spring 32 is disposed on push rod 29 so as to interface with disposable dome 60 and provide the mechanism for movement of indicator nut 30 in a linear manner by a predetermined amount when dome 60 is removed and replaced after each use of apparatus 10. The advancement of indicator nut 30 along push rod 29 thus provides a visual indication of the number of uses of apparatus 10.

Other usage indicating means may also be employed such as electronic proximity detection and display devices, rotary switches (standard or customized), and other such devices which may be activated through the engagement action or an independent operation by the user. One example of an alternative embodiment of a usage indicator that can also be used in the present invention is described hereafter.

A pressure sensing means such as a pressure transducer sensor 34 is disposed between back plate 22 and face plate 50 for producing electrical signals proportional to fluid pressures sensed in fluid-pathway 70. In one preferred embodiment, pressure transducer sensor 34 comprises a semiconductor integrated circuit chip that includes electronic components that form the sensor. The pressure transducer sensor 34 also includes a reusable diaphragm 36 that is configured to be flexed by fluid pressure pulses from fluid pathway 70.

Figure 5:
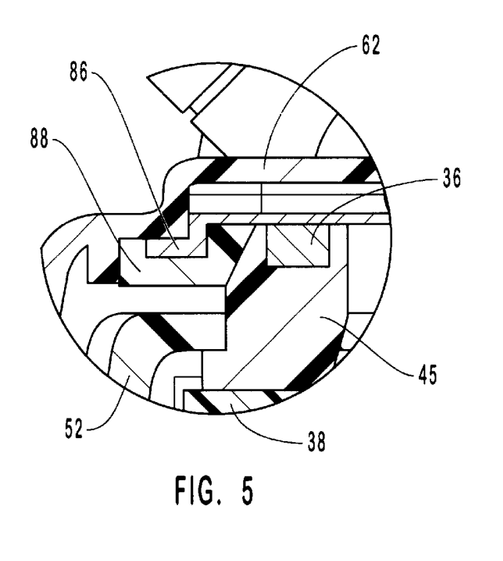
FIG. 5 is an enlarged sectional view of the blood pressure monitoring apparatus taken along line 5—5 of FIG. 4.

The pressure transducer sensor 34 is mounted on a substrate 38 such as a ceramic plate. The substrate 38 preferably includes integrated thick film circuitry that is capable of providing temperature drift correction, thereby improving sensor accuracy. A group of lead wires 40, which extend from substrate 38 into an electrically insulated cable 42, operatively connect sensor 34 to a display device (not shown). The cable 42 protrudes through an opening which is defined by matching groove portions 44a and 44b in back plate 22 and face plate 50, respectively. Further details of the components of sensor 34 and the surrounding housing structure are shown in FIGS. 4 and 5. FIG. 5 is an enlarged sectional view of monitoring apparatus 10 as depicted in FIG. 4. The sensor 34 includes a bowl-shaped member 45 that sits atop substrate 38. The bowl-shaped member 45 is commonly referred to as a gel cup. This gel cup contains a non-compressible pressure transmitting agent, such as a silicone gel, oil, or the like, which protects diaphragm 36 and acts as a dielectric barrier providing electrical isolation to the sensor electronics. The non-compressible pressure transmitting agent such as silicone gel also provides a fluid coupling mechanism with respect to the pressure pulses that are sensed through a fluid column in fluid pathway 70 during operation of the device.

The sensor 34 is pre-calibrated following the placement of reusable diaphragm 36 thereon, which allows for more accuracy in the overall performance of the device. For example, laser trim calibration can be performed for the sensor prior to final packaging, through which added accuracy of the sensing element is ensured over conventional sensor devices. It is known that sensor performance can have a wide range of drift with temperature and loss of sensitivity due to the large variation in the effects of adding the diaphragm to the sensor. By performing pre-calibration with the reusable diaphragm attached, and with the inclusion of external circuitry specifically designed to correct temperature errors as an integral part of the sensor design, superior accuracy can be obtained prior to final assembly in addition to minimizing the cost associated with yield loss due to sensor performance.

During construction of the sensor of the present invention, the larger diameter gel cup is filled with a suitable gel, following which the reusable diaphragm is attached to the gel cup in a batch multi-up form. Following calibration, there are no additional modifications that need to be done to the sensor that will shift performance. For example, in prior sensors it was often necessary to add a secondary gel cup extension. The present sensor avoids the additional step and expense of adding such a secondary gel cup. Since the effects of adding a reusable diaphragm are incorporated into the original calibration, higher performance and less yield loss are achieved with the sensor of the invention.

As shown in FIG. 6, face plate 50 has a box structure 52 protruding from an upper surface 53 for holding sensor 34 in a sensor chamber defined by box structure 52. A circular aperture 54 in box structure 52 is configured to allow reusable diaphragm 36 to protrude therethrough to receive pressure pulses from fluid pathway 70. A rectangular opening 56 in upper surface 53 preferably has a transparent covering thereover and serves as a viewing window for usage indicator 28. A predetermined color scale (not shown) can be placed next to the viewing window and pre-calibrated in such a way that the usage indicator will stay, for example, in a green region of the color scale when the base section is still reusable, and will move into a red region of the color scale when the base section has exceeded the recommended number of uses. Additional receiving apertures 57 and 58 formed in upper surface 53 are configured to receive corresponding mating members described in further detail below.

Figure 7:
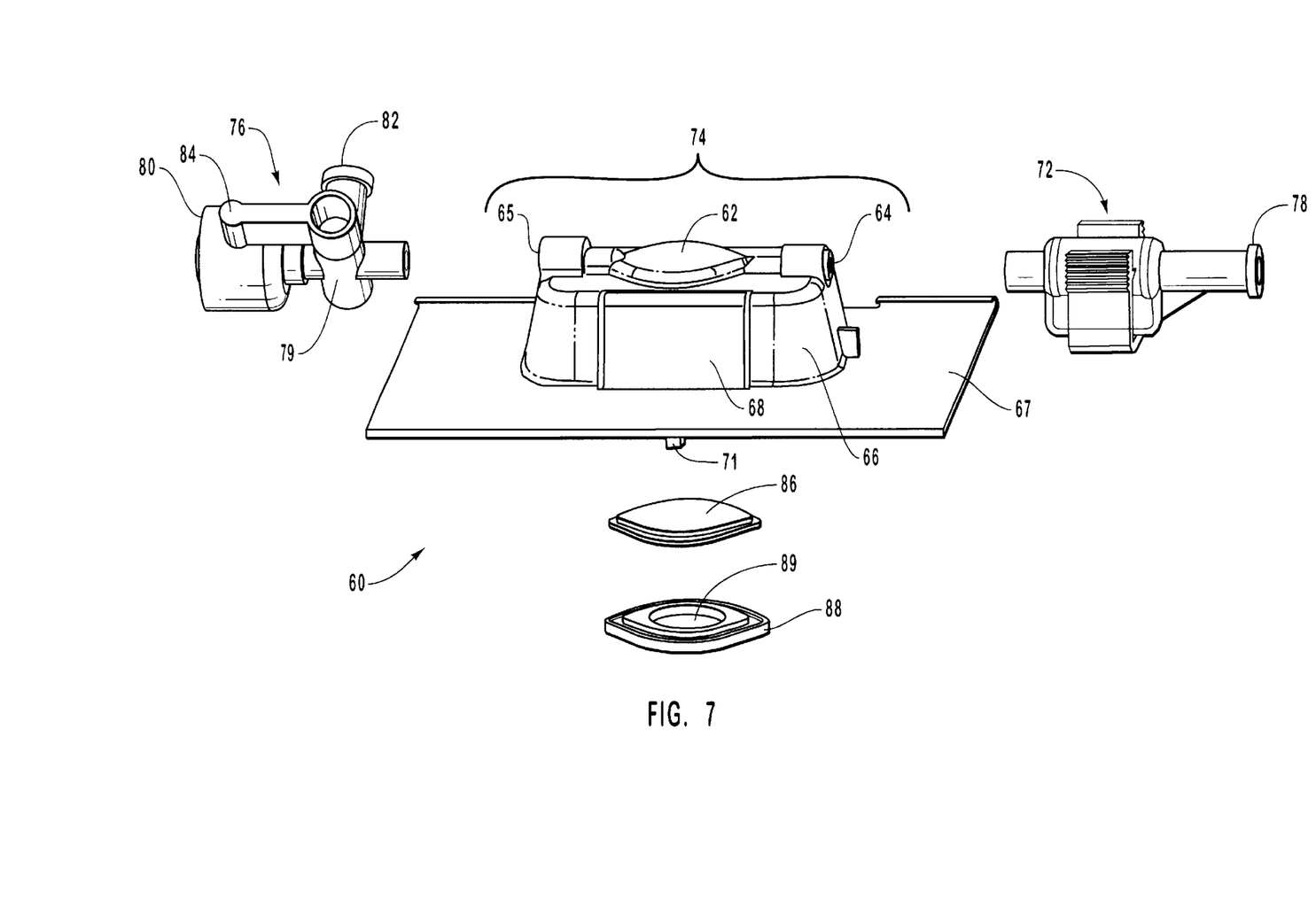
FIG. 7 is an exploded view of the disposable dome section of the blood pressure monitoring apparatus of FIG. 1.

The disposable dome section 60 of monitoring apparatus 10 is depicted in FIG. 7, and is formed from translucent or clear plastic by conventional molding techniques. The dome section 60 includes a fluid dome 62, which is preferably ellipsoidal in shape to enhance fluid visibility. The ability to view the fluid aids in the prevention of the introduction of air bubbles into a patient's bloodstream. The dome section 60 includes a saline input port 64 and an output port 65 which are in fluid communication with fluid dome 62. The fluid dome 62, input port 64 and output port 65 can be integrally formed as part of a dome housing 66, which is in turn located on a cover plate 67. The fluid dome 62, input port 64 and output port 65 define dome viewing segment 74 which provides a central portion of fluid pathway 70 as shown in FIG. 3.

As shown in FIGS. 2 and 7, dome section 66 has a flexible latch member 68 that is configured to mate with receiving aperture 58 in base section 20 in a snap fit arrangement so that a ridge 69 on latch member 68 engages a sidewall of aperture 58 in a self-registering, audible manner. This structure cooperates with the previously described hinge structures to form a self-registering "hinge and latch" structure used to attach dome section 60 to base section 20.

The cover plate 67 has a rigid protrusion 71 formed thereon that mates with receiving aperture 57 when dome section 60 is closed over base section 20. The protrusion 71 interacts with usage indicator 28 to cause incremental movement of indicator nut 30 along push rod 29 when a new dome section is attached to base section 20.

As discussed previously, the fluid pathway 70 is also defined by flush segment 72 and stopcock segment 76. The flush segment 72 is configured for coupling with input port 64 to provide part of fluid pathway 70, as shown in FIG. 3. The flush segment 72 has a fitting 78, such as a threaded female luer fitting, which provides for coupling of pressure tubing to the device. During set up of apparatus 10, flush segment 72 is used to flush fluid pathway 70 with a saline solution.

The stopcock segment 76 is configured for coupling with output port 65 to provide an additional portion of fluid pathway 70, which allows for subsequent fluid communication with a patient's blood stream during operation of apparatus 10. The stopcock segment 76 includes a three-way valve 79, which can be used to allow either saline solution to flush through fluid pathway 70 or to induce blood to flow from a catheter which has been inserted into the patient's blood stream. The stopcock segment 76 has a fitting 80, such as a rotatable threaded male luer fitting, which provides for coupling of pressure tubing to the device. The stopcock segment 76 also has an auxiliary port 82, which provides access to fluid pathway 70 while apparatus 10 is connected to a patient. A conventional syringe (not shown) can be attached to auxiliary port 82 for withdrawl of fluid from apparatus 10. An indicator handle 84 is operatively connected with three-way valve 79 to allow the practitioner to manually change the fluid path between auxiliary port 82 and fitting 80 in communication with a catheter.

The fittings 78 and 80 provide for coupling of apparatus 10 to pressure tubing of a type which is commonly known and used in the art in connection with hemodyamanic blood pressure monitoring systems or other similar types of pressure monitoring systems. In the case of hemodynamic blood pressure monitoring systems, fitting 80 will typically be connected through tubing to a catheter which is inserted into the patient for purposes of either arterial or venous blood pressure monitoring.

FIG. 7 additionally shows a disposable diaphragm 86 and a diaphragm retaining ring 88 which are disposed in dome housing 66 under fluid dome 62. Further details of disposable diaphragm 86 and diaphragm retaining ring 88 are shown in FIG. 5. The retaining ring 88 has a circular aperture 89 therethrough with a diameter slightly larger than reusable diaphragm 36, allowing reusable diaphragm 36 to abut against disposable diaphragm 86 in a confronting relationship when apparatus 10 is assembled. The diaphragm retaining ring 88 is configured to support disposable diaphragm 86 such that diaphragm 86 forms the lower wall of fluid pathway 70 in fluid dome 62.

The various components described above for apparatus 10 can be molded from plastic materials by conventional injection molding techniques. The formed components are then assembled together and secured by ultrasonic or other suitable forms of bonding to form the completed apparatus.

During clinical operation, apparatus 10 is connected at fitting 80 to pressure tubing that in turn is connected to an indwelling catheter (not shown) or the like, which is filled with a fluid column to measure blood pressure. The fluid column can constitute a liquid such as sterile saline solution, contrast media, or other similar kinds of liquids which are used to transmit fluid pressures that are to be monitored in fluid pathway 70. The apparatus 10 is also connected at fitting 78 to pressure tubing that is in communication with a source of saline solution (not shown). The fluid column is primed and de-bubbled and the apparatus is zeroed before use.

After use of apparatus 10 is complete, reusable base section 20 is easily separated from dome section 60 which is disposed of in an appropriate manner. A new disposable dome section can be subsequently attached to base section 20, and usage indicator 28 provides an incremental visual indication of base section usage. The operator is thus able to determine whether the number of uses is within the specified recommended limit. For example, when a color scale is used next to the indicator and the indicator moves to a red area, replacement of the reusable base section with a new base section is recommended.

Figure 8:
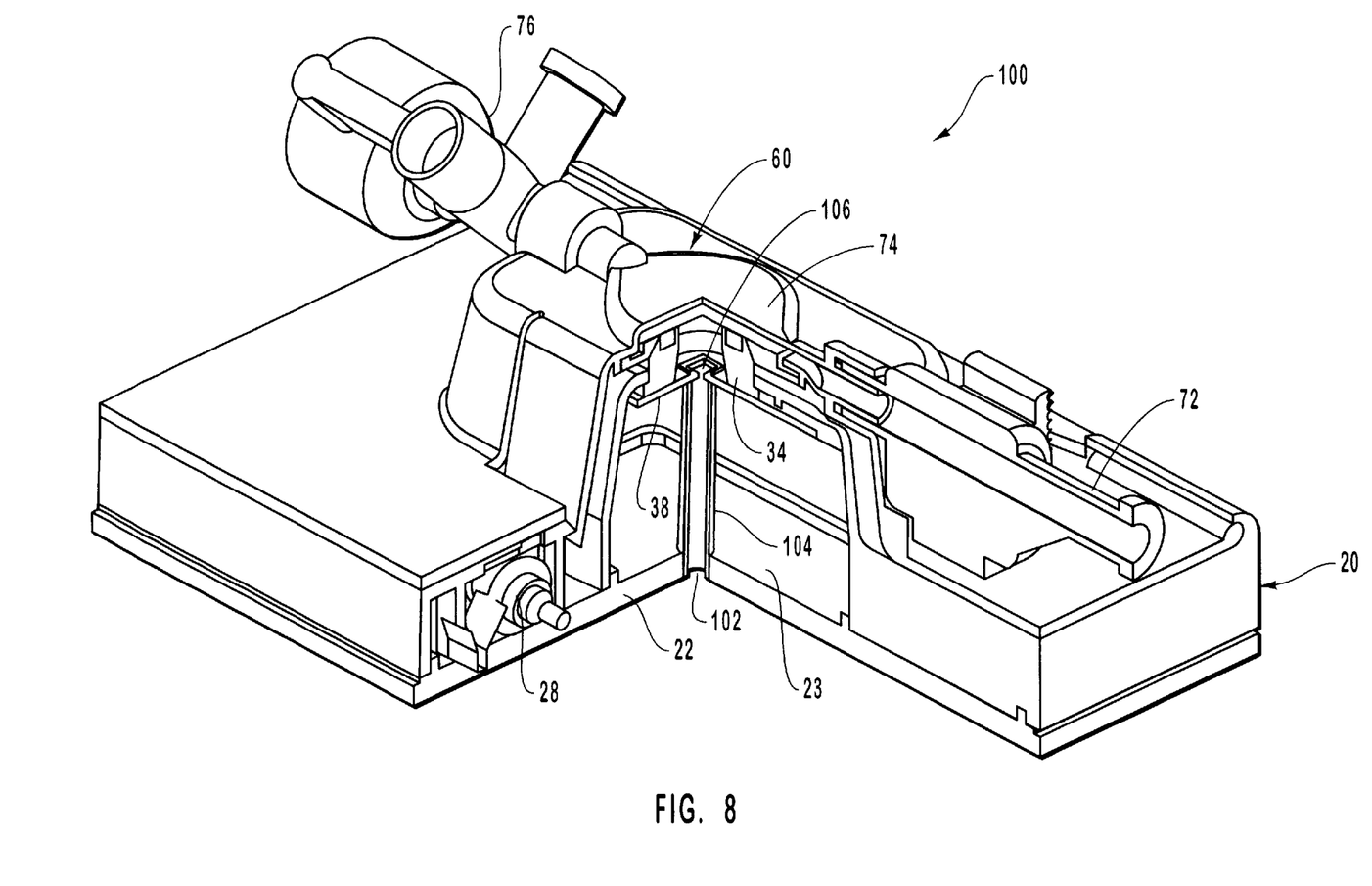
FIG. 8 is a perspective sectional view of a blood pressure monitoring apparatus in accordance with an alternative embodiment of the present invention.

FIG. 8 is a perspective sectional view of a blood pressure monitoring apparatus 100 in accordance with an alternative embodiment of the present invention. The monitoring apparatus 100 generally includes components similar to those described above for apparatus 10, including a reusable base section 20 and a disposable dome section 60, which is detachable from base section 20 and is generally intended for one time use. A mechanical usage indicator 28 and a pressure transducer sensor 34 as described previously are disposed in base section 20 of apparatus 100. The dome section 60 includes a flush segment 72, a dome viewing segment 74, and a stopcock segment 76, which are the same as the corresponding components described previously for apparatus 10.

In addition, apparatus 100 includes a calibration means for optimizing the pressure sensor. In one embodiment, the calibration means includes a backside calibration port 102 formed in a back plate 22 of base section 20. The calibration port 102 is used to introduce calibration pressures to the backside of the reusable diaphragm of the pressure sensor. The calibration port 102 is in communication with a calibration tube 104, such as a flexible tube, which is affixed at one end to a planar surface 23 over port 102 and at the other end to a substrate 38 of sensor 34. A calibration hole 106 is formed in substrate 38 and communicates with tube 104. A pressure generating device (not shown) can be coupled to port 102 to allow a user to perform functionality and calibration testing conveniently without violating fluid path sterility. For example, backside pressure may be applied through port 102 such as by a fluid filled syringe or other pressure inducing device to sensor 34. This allows a user to perform functionality and/or calibration tests which are known in the art and are also described, for example, in U.S. Pat. No. 5,273,047, the disclosure of which is incorporated by reference herein.

The backside calibration structure of apparatus 100 provides the advantage of not having to hermetically seal the base section 20. This is an advantage over conventional blood pressure transducer devices having backside calibration structures which require hermetic seals, as the failure of hermetic seals is a major source of yield loss of such conventional devices.

In an alternative embodiment, a flexible tube 104 may be employed in such a manner in apparatus 100 that a calibration port 102 may be positioned on the side or front face plate of the reusable component for convenient and easier access by the user.

Other examples of functionality testing that can be used with the device of the present invention include the user simply tapping the reusable diaphragm and observing a corresponding pressure response on an attached monitor. Additionally, an elastomer snap tab may be integrated into the disposable fluid path that will generate a square pressure wave when snapped by the user, thus providing an indication of proper dynamic response.

Figure 9:
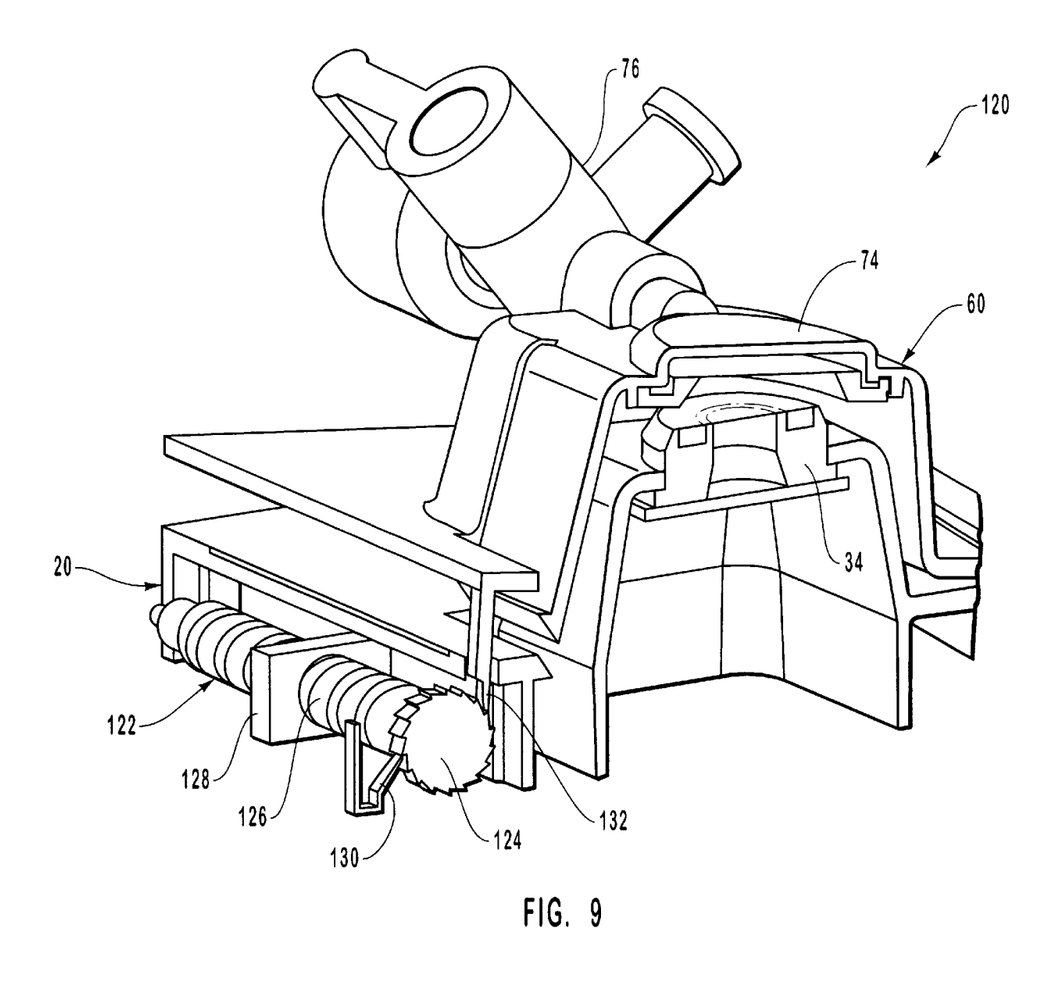
FIG. 9 is a perspective sectional view of a blood pressure monitoring apparatus in accordance with a further alternative embodiment of the present invention.

FIG. 9 is a perspective sectional view of a blood pressure monitoring apparatus 120 in accordance with a further alternative embodiment of the present invention. The monitoring apparatus 120 generally includes components similar to those described above for apparatus 10, including a reusable base section 20 and a disposable dome section 60, which is detachable from base section 20. A pressure transducer sensor 34 as described previously is disposed in base section 20 of apparatus 120. The dome section 60 includes a flush segment (not shown), a dome viewing segment 74, and a stopcock segment 76, which are the same as the corresponding components described previously for apparatus 10.

In addition, apparatus 120 includes a mechanical usage indicator 122 which is another example of a means for indicating usage of the device. The usage indicator 122 includes a toothed gear 124 mounted to a threaded shaft 126. An indicator nut 128 rides on threaded shaft 126 and advances therealong with each insertion of a new disposable dome 60. A spring 130 is engaged with toothed gear 124 to prevent backward motion of indicator nut 128 when disposable dome 60 is disengaged from apparatus 120. This prevents possible intentional or inadvertent tampering with the usage indicator reading. Such a configuration can also be used to prevent further usage if the device has reached its recommended limit of uses. A protrusion 132 on the dome section engages and rotates toothed gear 124 to cause incremental movement of indicator nut 128 along threaded shaft 126 when a new dome section is attached to base section 20. The movement of indicator nut 128 provides a visual indication of the number of uses of apparatus 120.

In an alternative embodiment, an o-ring can be used in place of the toothed gear in apparatus 120, but without the aspect of user lockout when the device has reached the limit for number of recommended uses.

As will be appreciated by those skilled in the art, while the present invention as illustrated and described is particularly useful for direct blood pressure monitoring, the present invention is not intended to be limited to that use and may be used in connection with other types of medical pressure monitoring applications, such as intra-cranial pressure monitoring. It will also be appreciated that non-medical applications may utilize the current invention where, for example, batch-to-batch contamination is avoided through employment of a disposable fluid path such as in chemical and food processing.

The present invention has many benefits and advantages over conventional reusable blood pressure monitoring devices. The increased visibility in the area of the disposable dome immediately above the dome to sensor interface aids the user in assuring air bubble elimination during the system saline fill process. The elongated shape of the fluid dome allows for such enhanced visibility.

The usage indicator which visually displays the number of uses of a reusable device substantially reduces the risk of unpredictable failure of the device. The usage indicator also greatly aids in inventory management, thus providing more predictability as to costs.

The sensor element used in the present invention requires no further adjustment for performance shifts that might otherwise occur during the assembly process with a conventional sensor. The sensor design accounts for packaging effects on performance at the time of packaging and enables multiple sensor testing at a single time which results in better device yields, lower manufacturing costs, and improved performance.

In addition, inclusion of a calibration port in some embodiments of the present invention allows calibration to be performed without violation of sterility. The present invention has the further advantage of allowing the calibration port to be configured on the side or front face plate of the reusable component to provide easier access for user interface.

The hinge and latch design of the present invention has the advantage of reducing the engagement mechanism to a single latch, which may be manipulated with one finger oriented generally parallel to the face plate, a substantial improvement for users with extended fingernails. For example, current iterations of two component systems incorporating a substantial reusable face plate utilize a dual latch engagement mechanism between disposable and reusable components. These latches are positioned on each side of a fluid dome in a generally parallel orientation to the flow of fluid such that user access to the latches is provided without interference with the stopcock/flush device and tubing protruding from both ends. To avoid interference with these protrusions while simultaneously activating both latches, it is necessary for the user to orient the thumb and index finger in or about a 90 degree orientation with respect to the face plate. For users with extended fingernails, proper contact with the latches is restricted through interference between fingernail and face plate, requiring awkward dexterity for manipulation of the engagement mechanism and/or the prospect of broken fingernails (a common complaint from nurses).

The hinge and latch interface as described in the present invention reduces the engagement mechanism to a single latch positioned on only one side of the fluid path. User interference with protrusions at both ends of the fluid path is avoided entirely, allowing users with extended fingernails to conveniently activate the engagement mechanism with a single finger oriented generally parallel to the faceplate such that interference with a fingernail is entirely avoided.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. An apparatus for monitoring fluid pressure, comprising:
    a reusable base section;
    a disposable dome section detachably connected to the base section, the dome section defining a fluid pathway;
    pressure sensing means disposed in the reusable base section for producing electrical signals proportional to fluid pressures sensed in the fluid pathway; and
    visual indicator means disposed in the base section for providing a visual indication of usage of the apparatus within a predetermined number of uses.

2. The apparatus of claim 1, wherein the base section includes a back plate and a face plate attached to the back plate.

3. The apparatus of claim 1, wherein the dome section is detachably connected to the base section by a releasable hinge and latch structure.

4. The apparatus of claim 3, wherein the hinge and latch structure includes at least one hinge rod on one edge of the dome section that is configured to releasably couple with at least one curved ridge on one edge of the base section, and a latch member on the dome section that is configured to mate with a receiving aperture in the base section in a snap fit arrangement.

5. The apparatus of claim 1, wherein the dome section comprises a translucent or clear plastic material.

6. The apparatus of claim 1, wherein the dome section includes a dome viewing segment in fluid communication with a flush segment and a stopcock segment.

7. The apparatus of claim 6, wherein the dome viewing segment includes a fluid dome having an ellipsoidal shape to enhance fluid visibility.

8. The apparatus of claim 1, wherein the pressure sensing means comprises a pressure transducer sensor disposed in a sensor chamber of the base section.

9. The apparatus of claim 8, wherein the pressure transducer sensor comprises a semiconductor integrated circuit chip and a reusable diaphragm that is configured to be flexed by fluid pressure pulses in the fluid pathway.

10. The apparatus of claim 9, wherein the pressure transducer sensor is mounted on a substrate that includes integrated thick film circuitry capable of providing temperature drift correction.

11. The apparatus of claim 10, wherein the pressure transducer sensor comprises a bowl-shaped gel cup that sits atop the substrate and supports the reusable diaphragm in a position adjacent to the fluid pathway.

12. The apparatus of claim 9, wherein the dome section further comprises a disposable diaphragm that is disposed under the fluid dome.

13. The apparatus of claim 12, wherein the disposable diaphragm is supported under the fluid dome and over the reusable diaphragm by a diaphragm retaining ring.

14. The apparatus of claim 13, wherein the diaphragm retaining ring is configured to support the disposable diaphragm such that the disposable diaphragm forms a lower wall for a portion of the fluid pathway which is under the fluid dome.

15. The apparatus of claim 13, wherein the diaphragm retaining ring defines a circular aperture with a diameter slightly larger than a diameter of the reusable diaphragm to allow the reusable diaphragm to abut against the disposable diaphragm.

16. The apparatus of claim 1, wherein the visual indicator means comprises a mechanical usage indicator disposed in the base section between the back plate and the face plate.

17. The apparatus of claim 16, wherein the mechanical usage indicator includes an indicator nut configured for incremental movement when the dome section is replaced after use with another disposable dome section that is attached to the base section.

18. The apparatus of claim 17, wherein the mechanical usage indicator includes a threaded cylindrical push rod on which is spring loaded the indicator nut.

19. The apparatus of claim 17, wherein the mechanical usage indicator includes a toothed gear mounted to a threaded shaft on which is spring loaded the indicator nut.

20. The apparatus of claim 16, wherein the mechanical usage indicator is visible through a window in the base section.

21. The apparatus of claim 17, wherein the dome section further comprises a rigid protrusion configured to mate with a receiving aperture in the base section when the dome section is attached to the base section.

22. The apparatus of claim 21, wherein the rigid protrusion interacts with the mechanical usage indicator to cause incremental movement of the indicator nut when the dome section is replaced after use with another disposable dome section.

23. The apparatus of claim 1, further comprising calibration means for optimizing the pressure sensing means.

24. The apparatus of claim 23, wherein the calibration means includes a backside calibration port in the back plate of the base section.

25. The apparatus of claim 24, wherein the calibration port is in communication with a calibration tube disposed in the base section and in pressure communication with the pressure sensing means.

26. An apparatus for monitoring blood pressure, comprising:

a reusable base section including a back plate and a face plate attached to the back plate;

a disposable dome section detachably connected to the base section and adapted to be coupled to a patient, the dome section defining a fluid pathway and including a dome viewing segment in fluid communication with a flush segment and a stopcock segment;

a pressure transducer sensor disposed in the reusable base section and adapted to produce electrical signals proportional to fluid pressures sensed in the fluid pathway;

a mechanical usage indicator disposed in the base section between the back plate and the face plate to provide a visual indication of usage of the apparatus within a predetermined number of uses; and calibration means for optimizing the pressure transducer sensor.

27. The apparatus of claim 26, wherein the dome section is detachably connected to the base section by a releasable hinge and latch structure.

28. The apparatus of claim 27, wherein the hinge and latch structure includes at least one hinge rod on one edge of the dome section that is configured to releasably couple with at least one curved ridge on one edge of the base section, and a latch member on the dome section that is configured to mate with a receiving aperture in the base section in a snap fit arrangement.

29. The apparatus of claim 26, wherein the dome viewing segment includes a fluid dome having an ellipsoidal shape to enhance fluid visibility.

30. The apparatus of claim 26, wherein the pressure transducer sensor comprises a semiconductor integrated circuit chip and a reusable diaphragm that is configured to be flexed by fluid pressure pulses in the fluid pathway.

31. The apparatus of claim 30, wherein the pressure transducer sensor is mounted on a substrate that includes integrated thick film circuitry capable of providing temperature drift correction.

32. The apparatus of claim 31, wherein the pressure transducer sensor comprises a bowl-shaped gel cup that sits atop the substrate and supports the reusable diaphragm in a position adjacent to the fluid pathway.

33. The apparatus of claim 30, wherein the dome section further comprises a disposable diaphragm that is disposed under the fluid dome.

34. The apparatus of claim 33, wherein the disposable diaphragm is supported under the fluid dome and over the reusable diaphragm in a confronting relationship by a diaphragm retaining ring.

35. The apparatus of claim 34, wherein the diaphragm retaining ring is configured to support the disposable diaphragm such that the disposable diaphragm forms a lower wall for a portion of the fluid pathway which is under the fluid dome.

36. The apparatus of claim 34, wherein the diaphragm retaining ring defines a circular aperture with a diameter slightly larger than a diameter of the reusable diaphragm to allow the reusable diaphragm to abut against the disposable diaphragm.

37. The apparatus of claim 26, wherein the mechanical usage indicator includes an indicator nut configured for incremental movement when the dome section is replaced after use with another disposable dome section that is attached to the base section.

38. The apparatus of claim 37, wherein the mechanical usage indicator includes a threaded cylindrical push rod on which is spring loaded the indicator nut.

39. The apparatus of claim 37, wherein the mechanical usage indicator includes a toothed gear mounted to a threaded shaft on which is spring loaded the indicator nut.

40. The apparatus of claim 26, wherein the mechanical usage indicator is visible through a window in the base section.

41. The apparatus of claim 37, wherein the dome section further comprises a rigid protrusion configured to mate with a receiving aperture in the base section when the dome section is attached to the base section.

42. The apparatus of claim 41, wherein the rigid protrusion interacts with the mechanical usage indicator to cause incremental movement of the indicator nut when the dome section is replaced after use with another disposable dome section.

43. The apparatus of claim 26, wherein the calibration means includes a backside calibration port in the back plate of the base section.

44. The apparatus of claim 43, wherein the calibration port is in communication with a calibration tube disposed in the base section and in pressure communication with the pressure transducer sensor.

45. An apparatus for monitoring fluid pressure, comprising:

a reusable base section;

a disposable dome section detachably connected to the base section, the dome section defining a fluid pathway;

pressure sensing means disposed in the reusable base section for producing electrical signals proportional to fluid pressures sensed in the fluid pathway; and a releasable hinge and latch structure for detachably connecting the dome section to the base section, the hinge and latch structure including one latch member on the dome section that is configured to mate with a receiving aperture in the base section.

46. The apparatus of claim 45, wherein the hinge and latch structure includes at least one hinge rod on one edge of the dome section that is configured to releasably couple with at least one curved ridge on one edge of the base section.

* * * * *

UNITED STATES PATENT AND TRADEMARK OFFICE
CERTIFICATE OF CORRECTION

PATENT NO. : 6,635,020 B2
DATED : October 21, 2003
INVENTOR(S) : Carl F. Tripp Jr., Mark A. Christensen and Eric Simon

It is certified that error appears in the above-identified patent and that said Letters Patent is hereby corrected as shown below:

<u>Title page,</u>
Item [56], References Cited, U.S. PATENT DOCUMENTS,
change "600/488" to -- 128/675 --;
change "604/151" to -- 248/221.3 --;
insert -- 5,359,993  11/94  Slater et al. --;
insert -- 5,991,355  11/99  Dahlke --;
insert -- 6,113,392  09/00  Braun --;
FOREIGN PATENT DOCUMENTS,
insert -- GB 2 342 752 A 04/00 United Kingdom --;
insert -- WO 00/61003 10/00 PCT --;
OTHER PUBLICATIONS,
change "Biotrans#" to -- Biotrans$^{TM}$ --;
change "Logical#" to -- Logical$^{TM}$ --;

<u>Column 6,</u>
Line 43, after "fluid" delete "-"

Signed and Sealed this

Thirtieth Day of March, 2004

JON W. DUDAS
*Acting Director of the United States Patent and Trademark Office*